(12) United States Patent
Motz (10) Patent No.: US 6,280,688 B1
(45) Date of Patent: Aug. 28, 2001

(54) RINSING DEVICE FOR SAMPLE PROCESSING COMPONENTS OF AN ANALYTICAL INSTRUMENT

(75) Inventor: Martin B. Motz, Cincinnati, OH (US)

(73) Assignee: Tekmar Company, Cincinnati, OH (US)

( * ) Notice: Subject to any disclaimer, the term of this patent is extended or adjusted under 35 U.S.C. 154(b) by 0 days.

(21) Appl. No.: 09/195,330

(22) Filed: Nov. 18, 1998

(51) Int. Cl.⁷ ............................... G01N 15/06; B08B 3/10
(52) U.S. Cl. ........................ 422/68.1; 422/50; 422/63; 422/81; 422/100; 422/103; 436/179; 436/180; 134/169 C; 134/170; 392/485; 392/486; 392/488; 392/489; 392/441; 392/445
(58) Field of Search ................. 422/63, 50, 81, 422/68.1, 100, 103; 436/180, 179; 134/169 C, 170; 392/485, 486, 488, 489, 441, 445

(56) References Cited

U.S. PATENT DOCUMENTS

| | | |
|---|---|---|
| 1,717,207 | 6/1929 | Halle . |
| 2,386,949 | 10/1945 | Hayward . |
| 2,594,616 | 4/1952 | Blondeau . |
| 2,607,878 | 8/1952 | Bowen . |
| 2,779,855 | 1/1957 | Sawyer . |
| 2,834,865 | 5/1958 | Coates . |
| 3,383,495 | 5/1968 | Laube et al. . |
| 3,484,580 | 12/1969 | Morgan . |
| 3,568,589 | * 3/1971 | Robau ..................... 99/283 |
| 3,787,659 | 1/1974 | Olland ..................... 219/314 |
| 3,945,411 | * 3/1976 | Skoli et al. .............. 141/91 |
| 4,310,010 | * 1/1982 | Svoboda ................... 134/135 |
| 4,323,760 | * 4/1982 | Greenway et al. ......... 219/364 |
| 4,514,617 | * 4/1985 | Amit ....................... 219/314 |
| 4,575,615 | 3/1986 | Shigenobu et al. ........ 219/314 |
| 4,835,365 | * 5/1989 | Etheridge ................. 219/298 |
| 4,858,155 | * 8/1989 | Okawa et al. ............. 364/557 |
| 5,042,293 | * 8/1991 | Heyde ..................... 73/61.1 |
| 5,108,705 | * 4/1992 | Rounbehler et al. ....... 422/89 |
| 5,324,480 | * 6/1994 | Shumate et al. ........... 422/63 |
| 5,387,334 | * 2/1995 | Kuroda et al. ............ 210/121 |
| 5,447,077 | * 9/1995 | Lautenschlager .......... 73/863.11 |
| 5,712,951 | 1/1998 | Chou ....................... 392/450 |
| 5,753,195 | * 5/1998 | Langford et al. .......... 422/292 |
| 5,858,114 | * 1/1999 | Board et al. .............. 134/18 |

* cited by examiner

*Primary Examiner*—Jan Ludlow
*Assistant Examiner*—Patricia Kathryn Bex
(74) *Attorney, Agent, or Firm*—Westman, Chaplin, & Kelly, P.A.

(57) ABSTRACT

A device for rinsing sample processing components of an analytical instruments including an inlet coupleable to a fluid source, an outlet coupleable to sample processing components of an analytical instrument, and a fluid reservoir between the inlet and outlet. The device includes a heater coupled to the fluid reservoir and the fluid reservoir includes at least two reservoir chambers connected in series and separated by a restricted passageway.

12 Claims, 11 Drawing Sheets

RINSING DEVICE FOR SAMPLE PROCESSING COMPONENTS OF AN ANALYTICAL INSTRUMENT

BACKGROUND OF THE INVENTION

The present invention relates to analytical instruments. In particular, the present invention relates to a rinsing device coupleable to an analytical instrument for rinsing sample processing components of the analytical instrument.

Analytical instruments are known which analyze various attributes of samples including liquid samples, such as drinking water or waste water samples and solid samples such as soil samples or gas samples. For example, such instruments may measure carbon content in water samples or volatile organic compounds (VOC) in soil samples.

Analytical instruments include autosamplers for systematically extracting samples for analysis, as well as purge and trap concentrators which are used with a liquid sample to prepare a gaseous sample for analysis by another analytical instrument such as a gas chromatograph. Such instruments may be connected for continuous operation for extracting, processing and analyzing samples.

During operation of an analytical instrument, sample may flow through sample processing components to extract a sample and process the sample for analysis. It is important to maintain a virgin sample for accurate measurement and analysis results. However, residue from prior samples can be deposited on the sample processing components and can be introduced in a subsequent sample thus contaminating the analysis of the subsequent sample. Thus it is desirable to remove residue from the sampling processing components prior to a subsequent testing cycle.

SUMMARY OF THE INVENTION

The present invention relates to a rinse device which intermittently provides heated rinsing fluid to the sample processing components for rinsing residue from a prior sampling cycle. The rinse device is a multi-stage heating apparatus including first and second reservoir chambers separated by a restricted passageway. Fluid is sequentially heated by the first and second reservoir chambers for discharge to rinse sampling processing components of an analytical instrument. The multi-stage heater improves temperature control for better temperature consistency for rinsing applications.

In one embodiment of the rinse device the reservoir includes a temperature sensor for controlling the temperature of the rinse fluid within the reservoir chambers. The sensor is coupled to a controller for energizing the heat source so that the temperature of the fluid in the reservoir is maintained within a desired temperature range for optimum effectiveness.

DETAILED DESCRIPTION OF THE PREFERRED EMBODIMENTS

Figure 1:
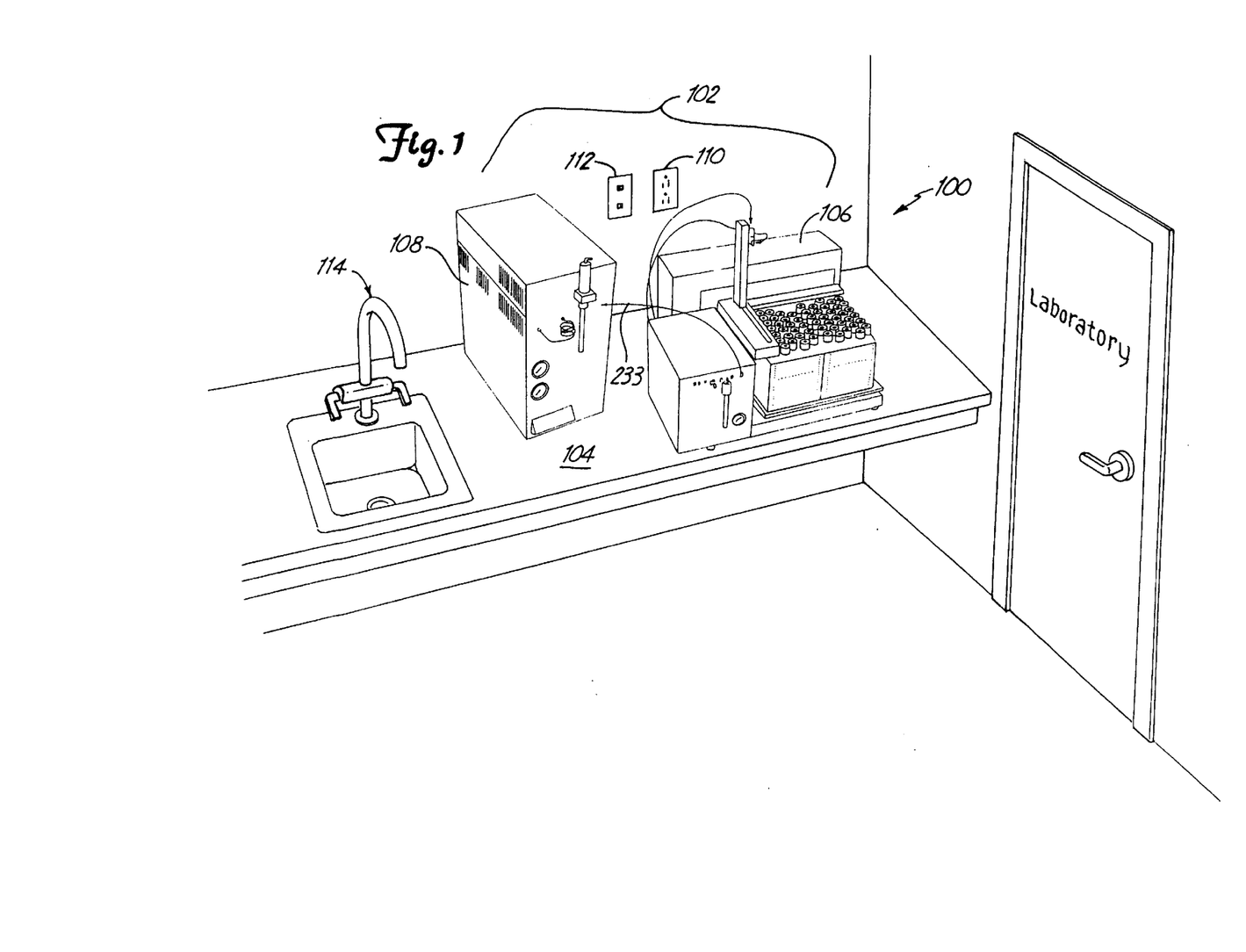
FIG. 1 illustrates a laboratory or testing facility environment.

FIG. 1 illustrates the environment of a version of the invention including a laboratory or research facility 100 and analytical instruments 102 supported on a lab bench 104. The analytical instruments illustrated in FIG. 1 include an autosampler 106 and a concentrator 108. The autosampler 106 extracts a sample. A concentrator 108 is coupled to the autosampler 106 to prepare a sample for analysis by a gas chromatograph (not shown) or similar apparatus.

As shown, laboratory facility 100 may be equipped with electrical outlets 110, a gas source 112 and a water source such as tap 114. The analytical instruments 102 are connected to the electrical outlets 110 for operating power. The autosampler 106 is coupled to a gas source 112 for supplying a carrier gas for sampling operation. The gas source can be a pressurized inert gas source such as helium. The gas can be contained in a standalone tank or can be contained in a permanent gas source structure.

Accurate analysis depends upon the integrity of the sample extracted, processed and delivered to the test apparatus for analysis. The analytical instruments 102 shown include sample processing components 118 as shown in FIGS. 2, 3, and 5–10. The sample processing components 118 carry or contain sample for processing and analysis and include sample tubes 122 (FIG. 5), and sample flow valves 124 (FIG. 5) and sample metering assembly or devices 126 (FIGS. 7–10), etc. If residue from a previous sample is left on the sample processing components 118, a subsequent sample can be contaminated and measurement accuracy of a subsequent sample can be compromised.

Figure 2:
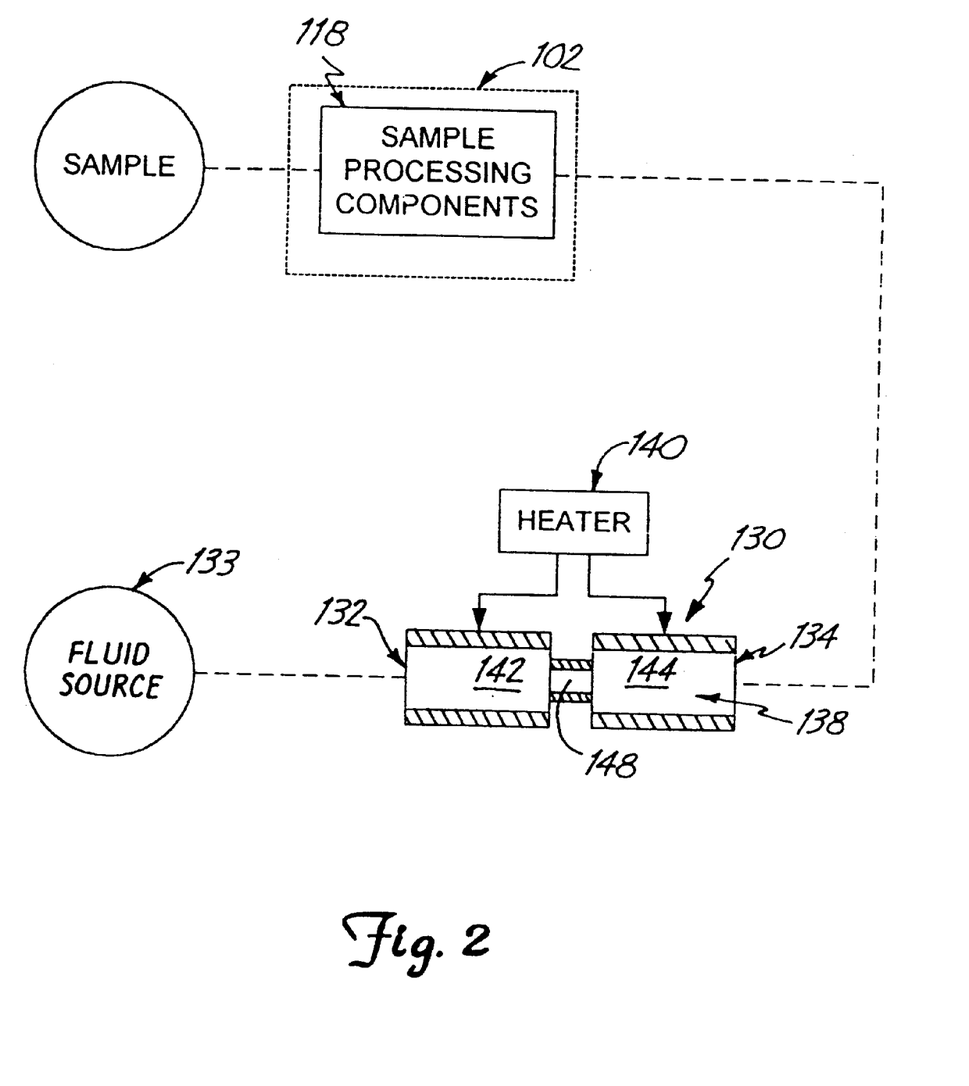
FIG. 2 is a schematic illustration of an embodiment of a rinse device coupled to sample processing components of an analytical instrument.

The embodiment in FIG. 2 relates to a device for rinsing sample processing components 118 of an analytical instrument 102 to eliminate residue from a prior sample. The rinse device 130 intermittently supplies rinse fluid to sample processing components 118 of the analytical instruments 102. The rinse device 130 includes inlet 132 coupleable to a fluid source 133, an outlet 134 coupleable to sample processing components 118 of an analytical instrument 102, a fluid reservoir 138 between the inlet and outlet 132, 134, and a heater 140 for heating fluid in the reservoir 138. As shown, the reservoir 138 includes two reservoir chambers 142, 144 connected in series and separated by a restricted passageway 148.

The fluid source 133 such as filtered tap water from water source 114 (FIG. 1)—filtered through a charcoal filter for example (not shown)—or deionized water from a tank such as a portable tank (not shown) provides rinse fluid heated by device 130. Alternate fluids may be used and use of the device is not limited to the specific fluids or mediums disclosed. Fluid is delivered to device 130 to elevate the temperature of the fluid within a defined temperature range for rinsing sample processing components 118. Fluid is delivered from fluid source 133 through inlet 132 to reservoir chamber 142. Fluid is heated in reservoir chamber 142. Fluid flows from reservoir chamber 142 through the restricted passageway 148 into reservoir chamber 144 connected in series with reservoir chamber 142. Fluid in reservoir chamber 144 is heated and discharged through outlet 134 to sample processing components 118 (including sample tubes 122, sample flow valves 124 (FIGS. 5 and 7–10) and sample metering assembly or devices 126 (shown in FIGS. 7–10) of an analytical instrument. Analytical instruments include autosamplers 106 and concentrators 108 as previously explained.

Figure 3:
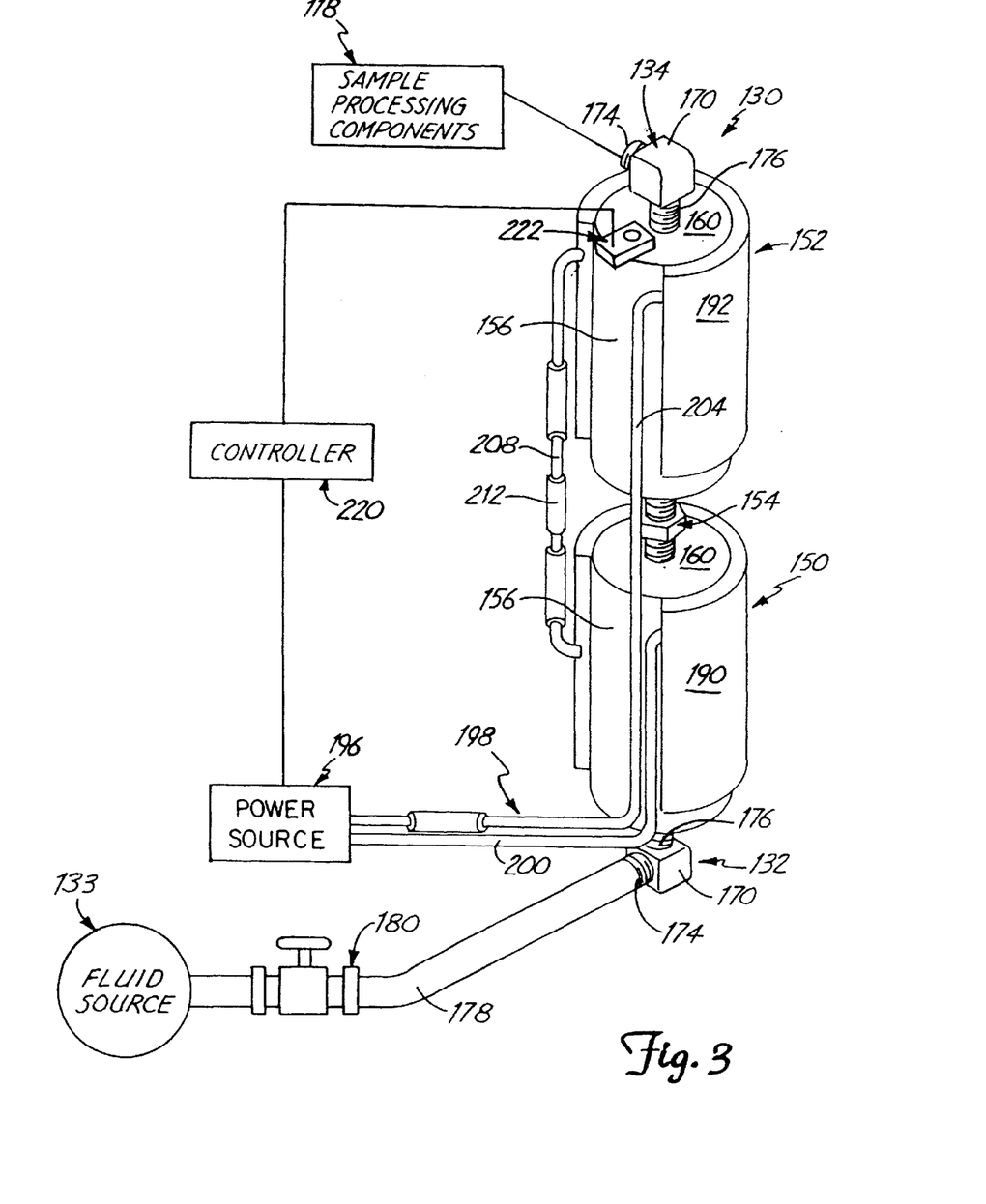
FIG. 3 is a perspective illustration of an embodiment of a rinse device.
Figure 6:
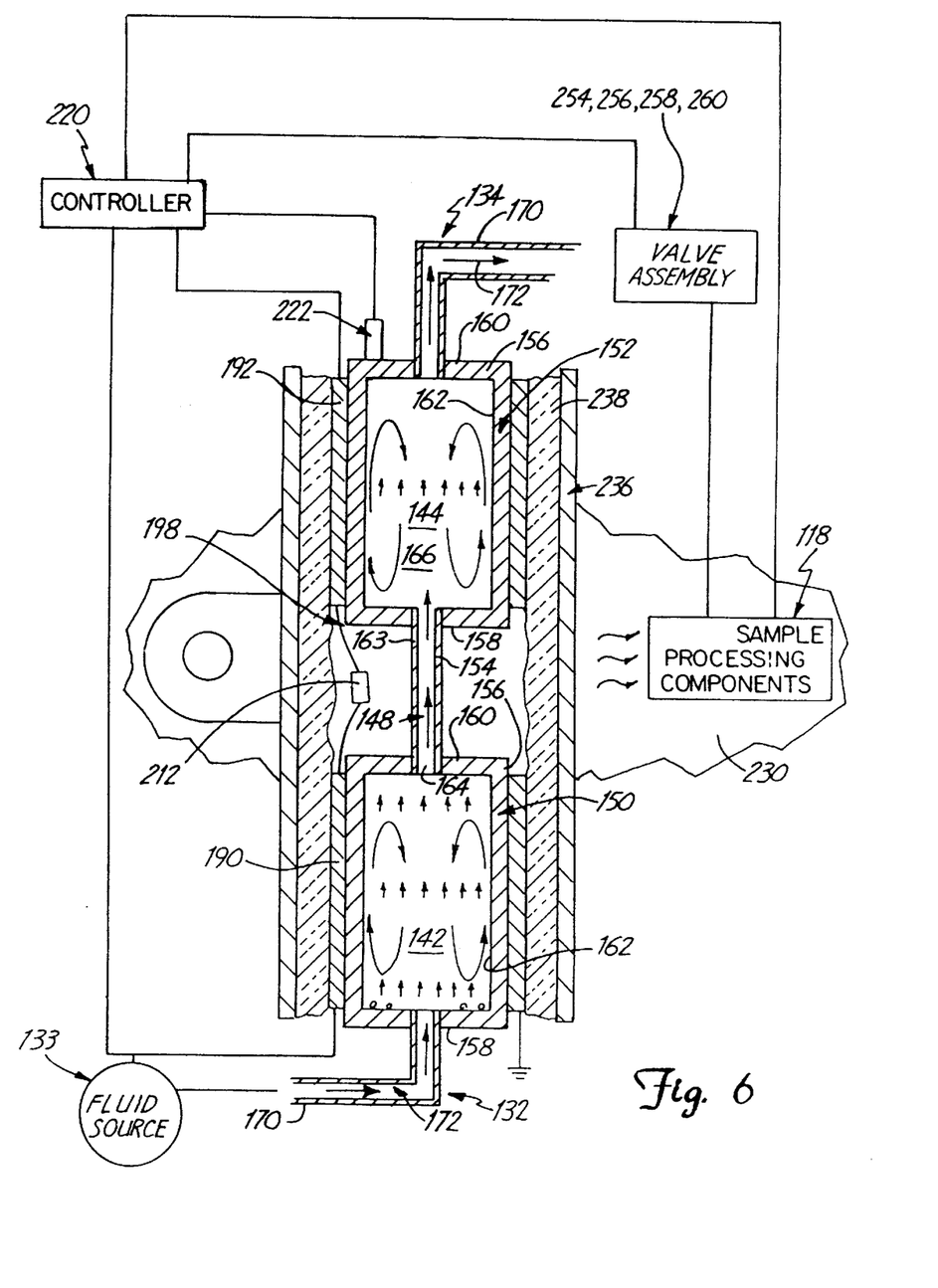
FIG. 6 is a cross-sectional view of an embodiment of the rinse device illustrated in FIG. 5.

The embodiment of the rinse device shown in FIGS. 3 and 6, has hollow elongated cylinders 150, 152 connected by a narrow tube 154 to form reservoir chambers 142, 144 and restricted passageway 148. In particular, the cylinders 150, 152 include an outer cylindrical wall 156 and opposed end walls 158, 160 (shown in FIG. 6) enclosing an interior chamber 162 (as shown in FIG. 6). Interior chambers 162 of members 150, 152 form the reservoir chambers 142, 144. Cylinders 150, 152 can be formed of a metal material able to withstand high temperatures. The capacity or volume of chambers 162 is sized to hold a sufficient volume of rinse fluid for multiple rinse cycles. For example, a single rinse cycle can require 25–40 milliliters of fluid and the capacity of the combined chambers 162 for cylinders 150, 152 can hold 140 milliliters of fluid.

Tube 154 includes an inner conduit 163 and opened threaded ends 164, 166 (shown in FIG. 6). Conduit 163 has a reduced cross-sectional area in comparison to the reservoir chambers 142, 144 to form the restricted passageway 148. The restricted passageway 148 is small enough to separate the reservoir chambers 142, 144 to limit significant intermixing of fluid so that unheated fluid from fluid source 133 introduced into chamber 142 does not sufficiently mix with fluid in the second reservoir chamber 144 to lower the elevated temperature of the fluid in the second reservoir chamber 144. Since fluid in reservoir chamber 144 is separated from unheated fluid from fluid source 133 by reservoir chamber 142 and restricted passageway 148, the temperature of fluid in reservoir chamber 144 is easier to control for better temperature consistency.

In the embodiment shown in FIG. 6, ends 164, 166 of the tube 154 are threadably attached to end walls 158, 160 of cylinders 150, 152 so that conduit 163 is opened or fluidly coupled to interior chambers 162 of cylinders 150, 152. Tube 154 is also formed of a material able to withstand high temperatures. The threaded ends 164, 166 are sealed by a Teflon tape to limit leakage.

In the embodiment shown in FIG. 3, inlet 132 and outlet 134 are formed of threaded couplers 170 having a fluid passageway 172 therethrough (shown in FIG. 6). The threaded couplers 170 include opposed threaded ends 174, 176. Threaded end 176 of the inlet 132 is coupled to end wall 158 of cylinder 150 and threaded end 174 is coupled to fluid source 133 via a hose 178. Threaded end 176 of outlet 134 is coupled to end wall 160 of cylinder 152 and threaded end 174 is coupleable to sample processing components 118. The threaded ends 174, 176 are sealed by a Teflon tape to limit leakage. In the embodiment shown in FIG. 3, a pressure relief valve 180 is coupled to the reservoir 138 (at inlet 132) via hose 178 to relieve pressure build up in the reservoir 138.

Heater 140 is coupled to and heats each reservoir chamber 142, 144 as previously illustrated in FIG. 2. In the embodiment illustrated in FIG. 3, heater 140 includes first and second conductive sleeves 190, 192 partially enclosing cylinders 150, 152. Heating elements in the sleeves 190, 192 are connected in series to a power source 196 via heating circuit 198 to provide an embodiment of heating members coupled to each reservoir chamber 142, 144. The heating circuit 198 includes a first wire 200 coupled between the power source 196 and a heating element in the sleeve 190. A second wire 208 is coupled between the heating element in the sleeve 190 and the heating element in sleeve 192. A third wire 204 is coupled between the heating element in sleeve 192 and the power source 196. A thermal circuit protector 212 is incorporated into the heating circuit 198 preferably between conductive sleeves 190, 192 to provide a circuit interrupt to protect components of the device from overheating. Although separate heating members are shown connected in series, a single heater or multiple heaters separately connected or connected in parallel could be used in addition to that shown.

In the embodiment of the rinse device illustrated in FIG. 3, operation of the heater 140 is controlled by a controller 220. Controller 220 operates heater 140 to provide adequate heat to maintain fluid temperature within a desired temperature range. The heater may be cycled on to initially heat incoming fluid and cycled off once the fluid is within the desired temperature range. In the embodiment shown a temperature sensor 222 is included for heater control.

The temperature sensor 222 senses the temperature in reservoir 138 (cylinder 152) in order to regulate the temperature of the fluid within reservoir 138. The temperature sensor 222 is coupled to the controller 220 to adjust the energization of heater 140 based upon the sensed temperature.

If the temperature is outside a predefined temperature range, the energization of the heater 130 is either increased or decreased to adjust the temperature of fluid in the reservoir 138 within the desired temperature range. The desired temperature range is below the boiling point of a rinsing fluid so that steam is not supplied to rinse the sample processing components 118. Example temperature sensors include a thermistor included as an integrated circuit, a thermocouple or other temperature sensor devices. The temperature sensor 222 is coupled to reservoir chamber 144 adjacent to or opened to outlet 134 for temperature control.

Figure 4:
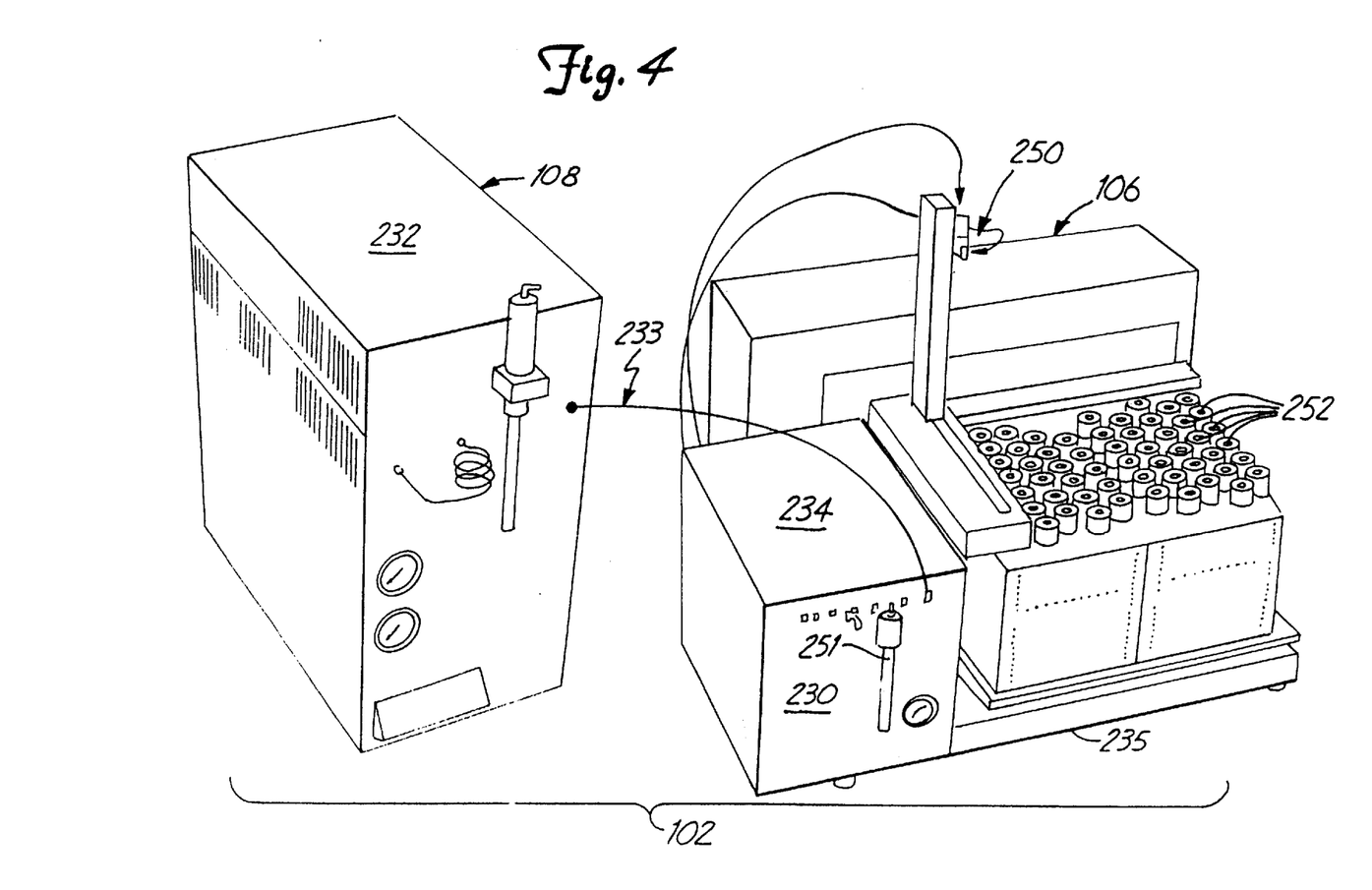
FIG. 4 is an enlarged perspective illustration of autosampler and concentrator units.

As described, reservoir chambers 142, 144 provide a multi-stage device for sequentially heating fluid from fluid source 133 for discharge to sample processing components 118. FIG. 4 is a detailed illustration of an analytical instrument 102 including separate autosampler and concentrator units 106, 108 having sample processing and operating components housed in cabinets 230, 232. Autosampler unit 106 shown in FIG. 4 measures and delivers the sample to concentrator unit 108 via line 233 coupled to the autosampler unit 106 and concentrator unit 108. Although shown as separate units, these components could be constructed as a single unit.

Figure 5:
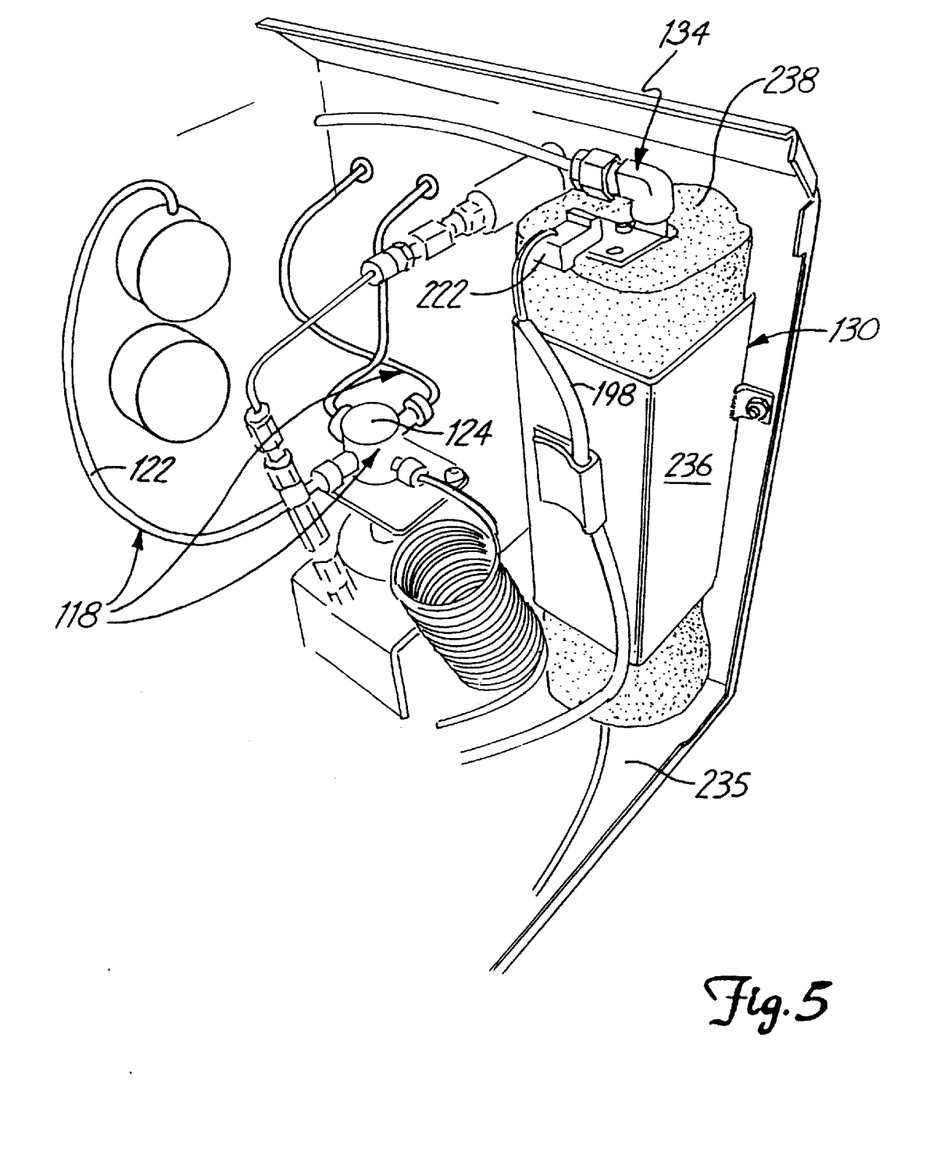
FIG. 5 is a detailed view of the autosampler unit with an outer cover removed to illustrate the sample processing components of the unit and rinse device.

In FIG. 5, a cover 234 (shown in FIG. 4) enclosing the autosampler unit 106 is removed to illustrate sample processing and other operating components. As previously explained, the sample processing components include sample tubes 122, sample flow valves 124, etc. In the embodiment shown, the rinse device 130 is supported in vertical alignment (generally perpendicular to a support base 235 of the device) via a bracket 236. An insulator member 238 surrounds or encloses a portion of the device 130. In one embodiment the insulating member 238 is foam, although other insulating materials may be used. The insulating member 238 or jacket restricts heat flow from the device 130 to conserve energy and protect other processing components from overheating.

FIGS. 7–10 are simplified schematic illustrations of an embodiment of components of an autosampler unit 106

(including sample processing components 118) and concentrator 108 interfaced with a rinse device 130. Rinse fluid is supplied from rinse device 130 to autosampler 106 and concentrator 108 for rinsing sample processing components 118 as will be explained. As shown, autosampler 106 includes a sampling needle 250, a standard vial 251, and valves 254, 256, 258 and 260 (forming a valve assembly) as shown in FIGS. 7–10. Sampling needle 250 extracts sample from vials 252 (shown in FIG. 4) for analysis by a gas chromatograph 253 for example coupled to the concentrator 108.

Valve 254 includes a normally closed port 262 coupled to rinse device 130 via conduit 264, a normally opened port 266 coupled to a pressurized carrier source 268 and a common port 270 coupled to a common port 272 of valve 256. Valve 256 includes a normally opened port 273 coupled to sampling needle 250 and a normally closed port 274 coupled to valve 258.

Valves 258 and 260 close ends of a measurement pipette 280 to form a sample metering assembly 126. Valve 258 includes port 282 opened to valve 256, port 284 normally opened to drain 285 and port 286 opened to pipette 280. Valve 260 includes port 290 coupled to sampling needle 250, port 292 opened to pipette 280 and port 294 fluidly coupled to the concentrator 108.

Figure 7:
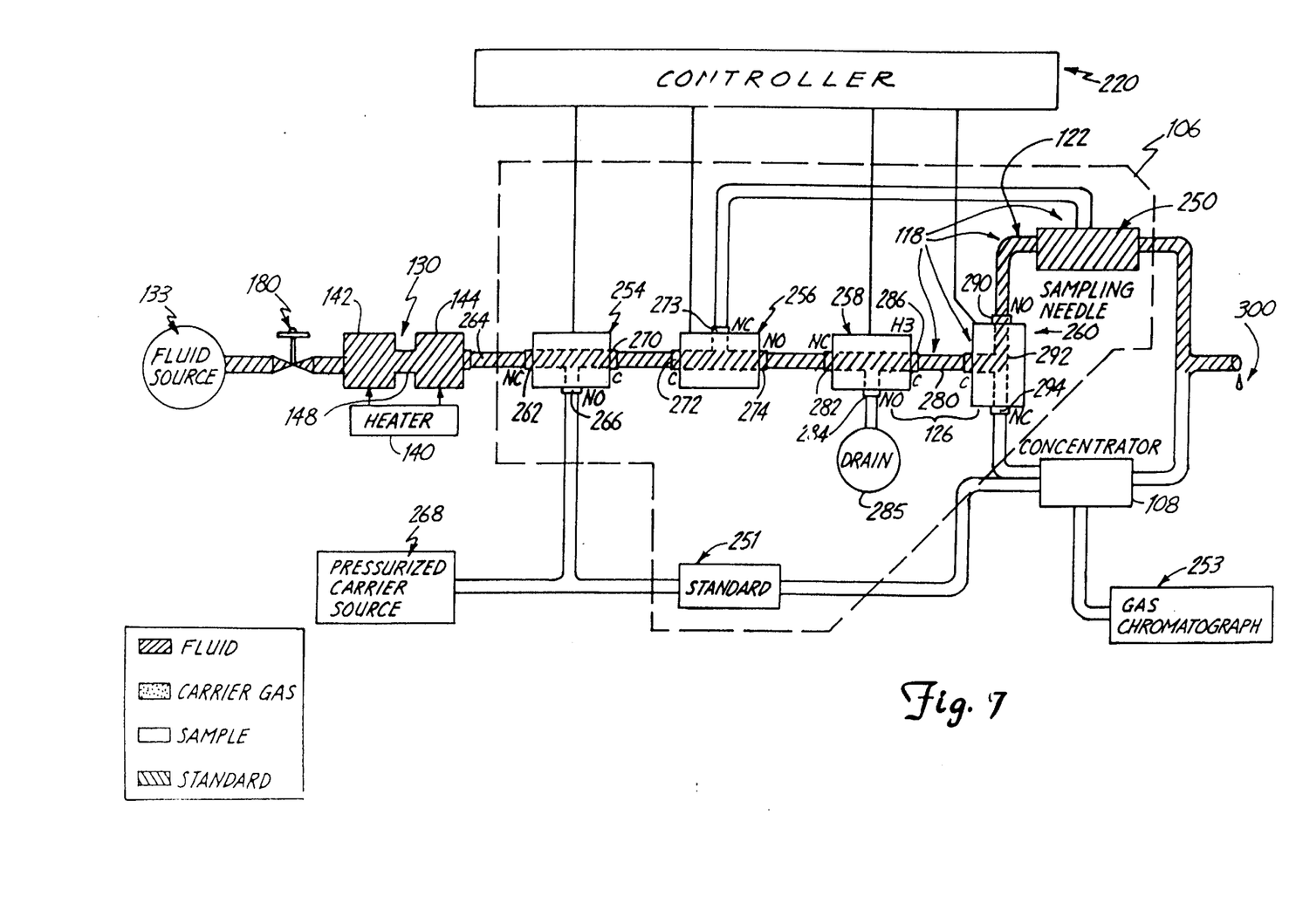
FIGS. 7–10 are simplified schematic illustrations of operation of the rinse device interfaced with sample processing components of an autosampler unit and concentrator unit.
Figure 8:
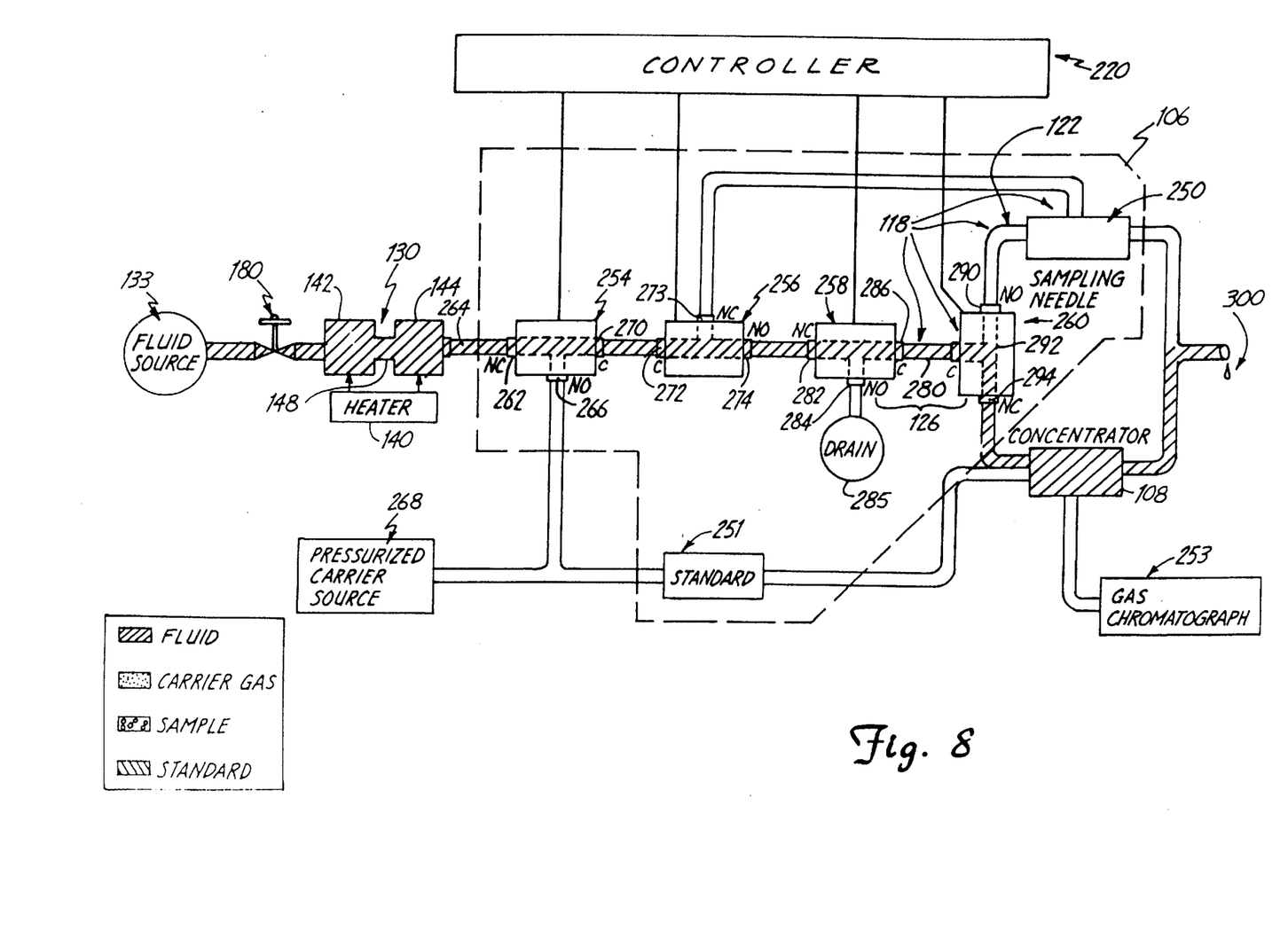

FIGS. 7-8 illustrate a rinse cycle of the apparatus. As shown, during a rinse cycle, normally closed port 262 of valve 254 is opened to allow rinse fluid to be discharged from device 130. Rinse fluid is directed through sample metering assembly (pipette 280) and sampling needle 250 as shown in FIG. 7 and through concentrator 108 as illustrated in FIG. 8 via selective operation of ports 290, 294 of valve 260. Rinse fluid is discharged to a drain 300.

Figure 9:
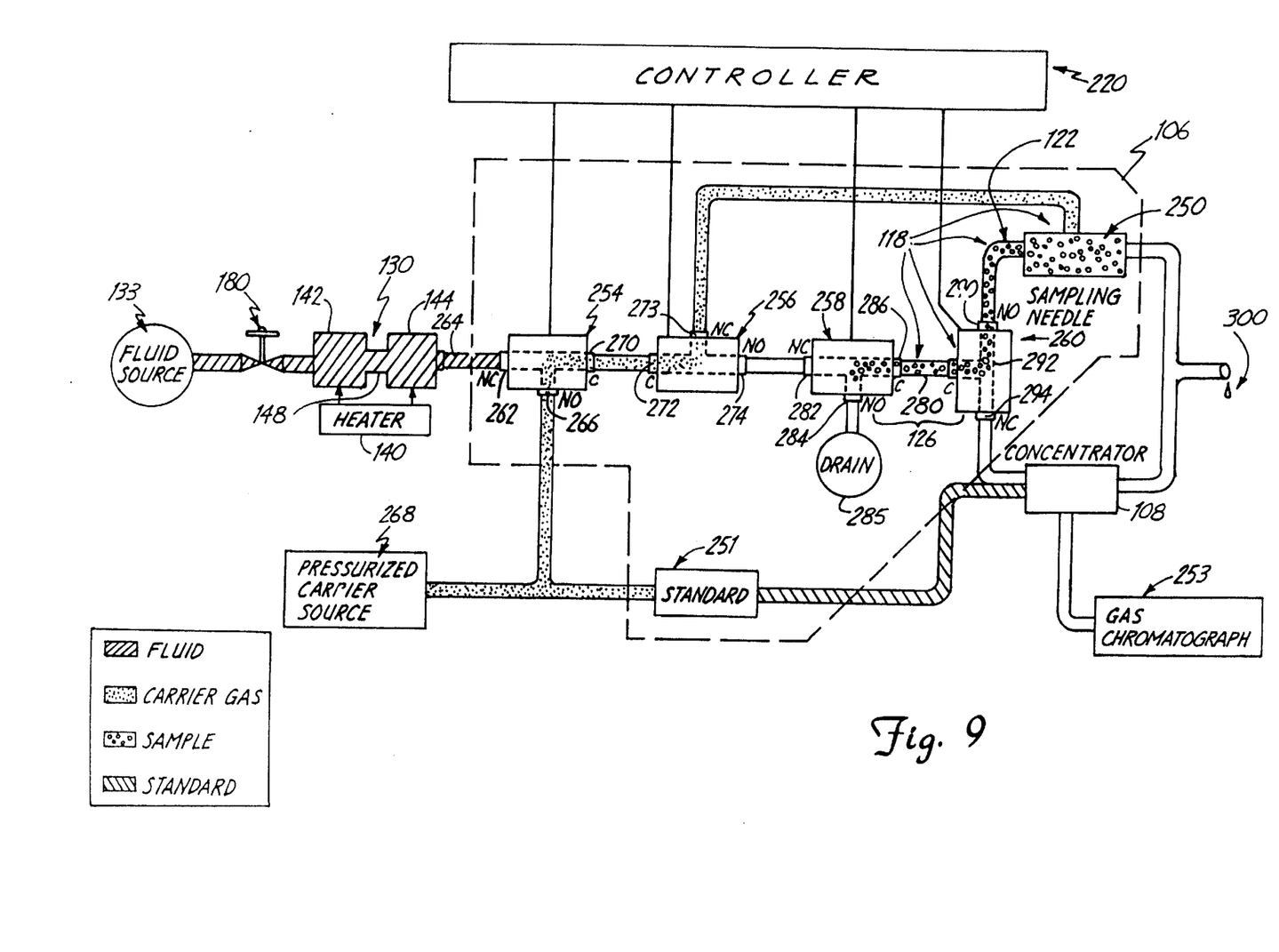

After completion of a rinse cycle valve port 262 is closed and port 266 is opened for continued sampling operation. During a sampling operation, normally closed port 273 of valve 256 is opened to supply pressure to sampling needle 250 to extract a sample. Valve port 290 is opened to fill pipette 280 for measurement as shown in FIG. 9. Standard 251 is supplied to concentrator 108 and port 282 is opened to carrier gas source 268 to empty sample from pipette 280 to concentrator 108.

Operation of valves 254, 256, 258 and 260 is controlled by controller 220 for continuous automated sampling operation and intermittent rinsing. Operation of valves 254, 256, 258 and 260 for various operations is summarized in the table below. The table identifies the opened valve ports for valves 254, 256, 258 and 260 for various operations. As illustrated, there are two rinse modes, RINSE I and RINSE II. During RINSE I (FIG. 7), sampling needle 250 is rinsed and during RINSE II FIG. 8), rinse fluid is supplied to the concentrator 108.

Figure 10:
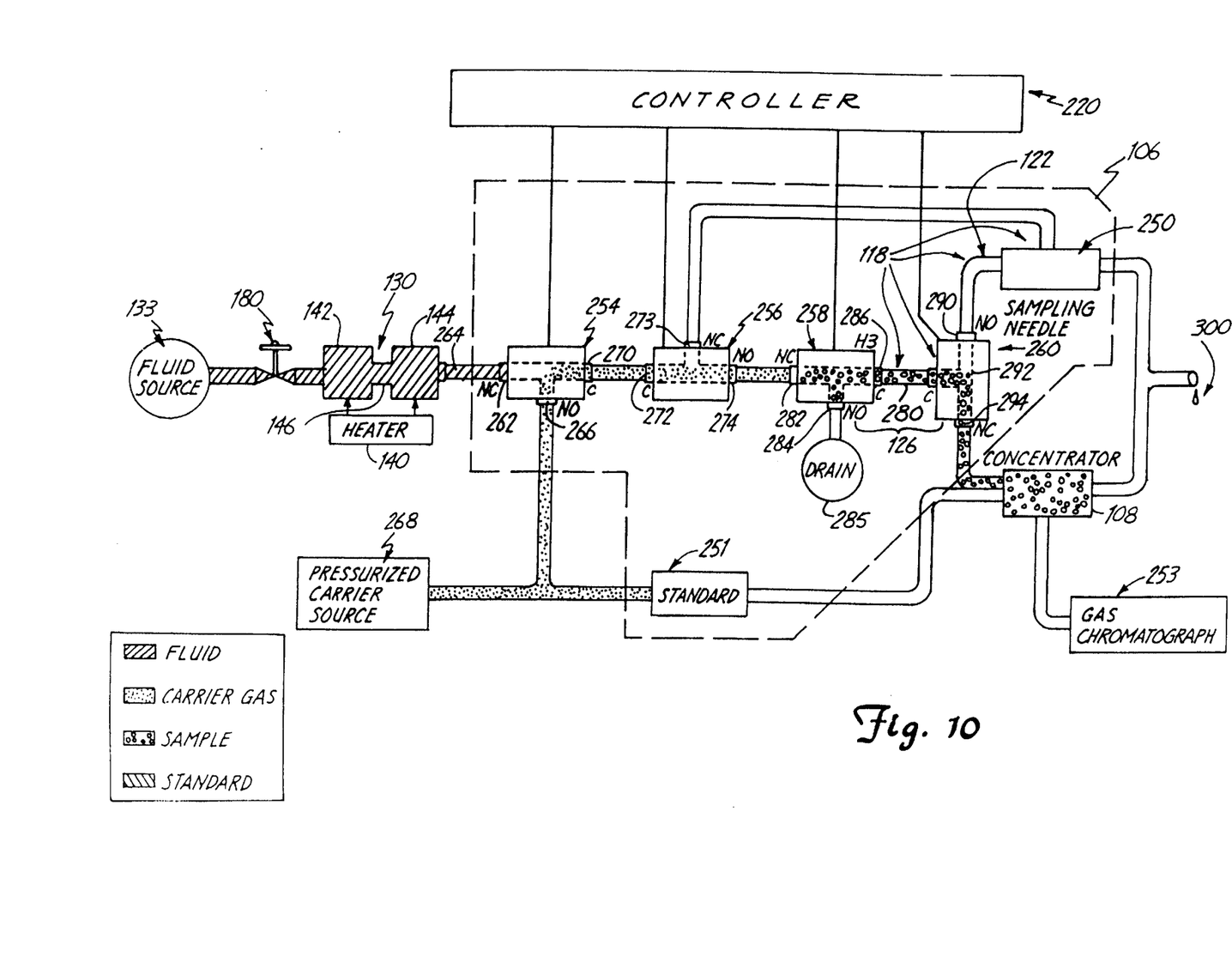

| | OPEN PORT ON VALVE | | | | |
|---|---|---|---|---|---|
| MODE | VALVE 254 | VALVE 256 | VALVE 258 | VALVE 260 | FIG. NO. |
| RINSE I | 262 | 274 | 282 | 290 | FIG. 7 |
| RINSE II | 262 | 274 | 282 | 294 | FIG. 8 |
| SAMPLE | 266 | 273 | 284 | 290 | FIG. 9 |
| GAS PURGE | 266 | 274 | 282 | 294 | FIG. 10 |

Figure 11:
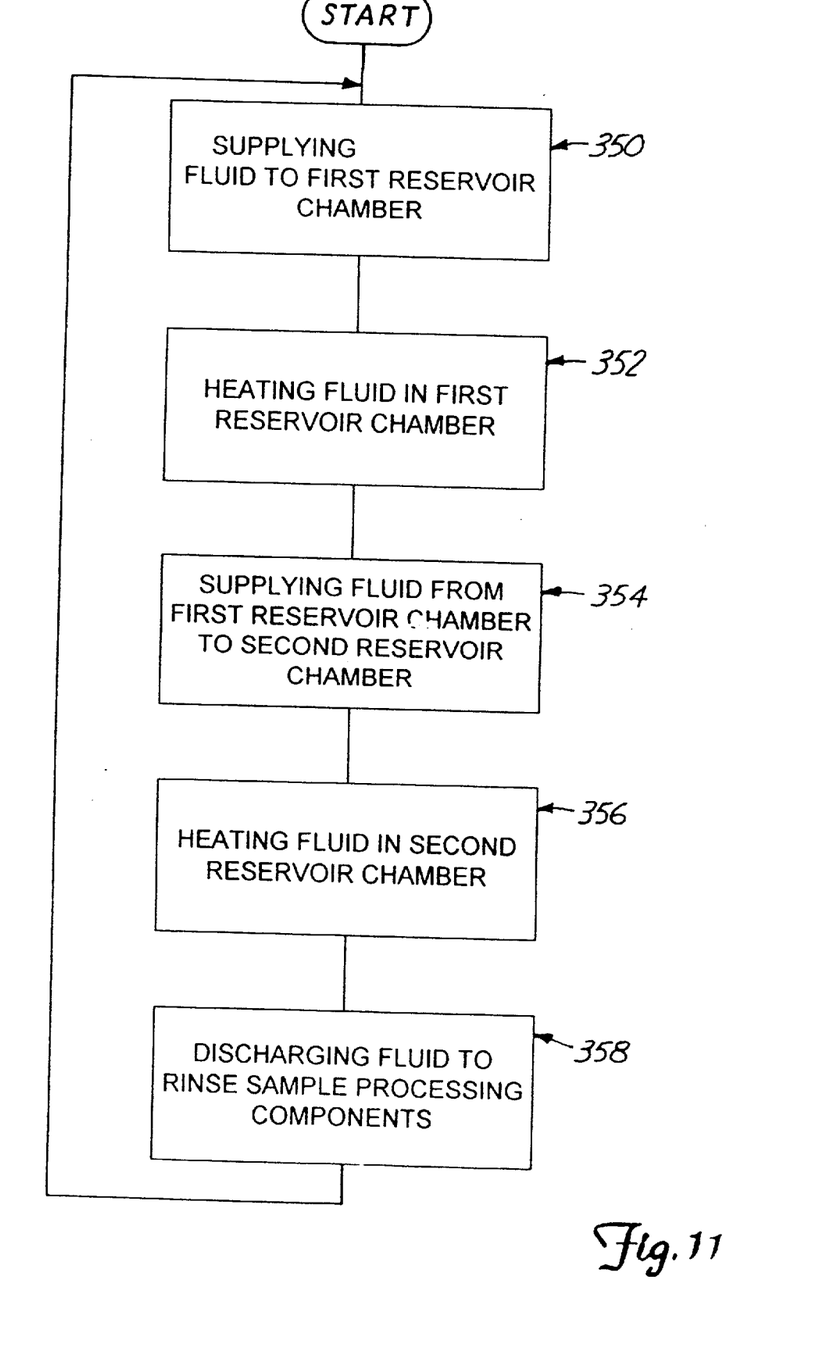
FIG. 11 is a flow diagram of operation of an embodiment of the rinse device.

As illustrated in FIG. 11, in operation, fluid is supplied to a first reservoir chamber 142 from a fluid source 133 and heated as illustrated by blocks 350, 352. Fluid from the first reservoir chamber 142 is supplied to the second reservoir chamber 144 through the restricted passageway 148 and heated as illustrated by blocks 354, 356 Fluid from the second reservoir chamber 144 is discharged (via port 262 of valve 254) to rinse sample processing components as illustrated by block 358. In an embodiment, the reservoir chambers are normally opened to the fluid source 133 and fluid is concurrently heated in the reservoir chambers 142, 144. Fluid is maintained in the reservoir chambers via valve 254 until needed for a rinse cycle after a sampling cycle.

On demand, fluid in the desired temperature range is available in the reservoir chambers and intermittently discharged for a rinse cycle when port 262 of valve 254 is opened. As fluid is discharged from the reservoir 138 (chamber 144), fluid from source 133 (normally open to the reservoir) flows into reservoir chamber 142 to fill a portion of the reservoir emptied to replenish fluid in the reservoir so that fluid is available for a subsequent rinse cycle. Since fluid is heated in multi-reservoir chambers, better temperature consistency is achieved.

Although the present invention has been described with reference to preferred embodiments, workers skilled in the art will recognize that changes may be made in form and detail without departing from the spirit and scope of the invention.

What is claimed is:

1. An analytical instrument comprising:
   a cabinet;
   sample processing components operably coupled to the cabinet;
   a fluid rinse device including an inlet and an outlet, the inlet being coupleable to a fluid source and the outlet being coupleable to the sample processing components;
   wherein the fluid rinse device includes a reservoir having at least two reservoir chambers connected in series and separated by a restricted passageway and a heater being disposed about an exterior of each reservoir chamber for heating fluid in the reservoir chamber;
   a valve assembly coupleable to a pressurized carrier source, the fluid rinse device, and sample processing components; and
   a controller coupled to the valve assembly to intermittently supply fluid to rinse the sample processing components.

2. The analytical instrument of claim 1 and including a bracket coupleable to the cabinet and adapted to support the fluid rinse device in vertical alignment generally perpendicular to a support base of the device.

3. The analytical instrument of claim 1 including an insulating member surrounding a portion of the fluid rinse device.

4. The analytical instrument of claim 1 wherein the sample processing components include a sample metering assembly.

5. The analytical instrument of claim 1 wherein the sample processing components includes a sample tube.

6. The analytical instrument of claim 1 wherein the sample processing components include a sample flow valve.

7. The analytical instrument of claim 1 wherein the sample processing components include a sampling needle.

8. The analytical instrument of claim 1 wherein the valve assembly comprises:
   a first port coupleable to the fluid rinse device;
   a second port coupleable to a pressurized carrier source; and an outlet port coupleable to the sample processing components wherein the controller operates the valve assembly to intermittently open and close the first and second ports.

9. The analytical instrument of claim 8 wherein the valve assembly includes an outlet port coupleable to a concentrator.

10. An analytical instrument comprising:

a cabinet;

sample processing components operably coupled to the cabinet;

a fluid rinse device including an inlet and an outlet, the inlet being coupleable to a fluid source and the outlet being coupleable to the sample processing components;

wherein the fluid rinse device includes a reservoir having at least two reservoir chambers connected in series and separated by a restricted passageway and a heater being coupled to each reservoir chamber for heating fluid in the reservoir chamber;

a valve assembly coupleable to the fluid rinse device, a pressurized carrier source and the sample processing components, the valve assembly including: a first port coupleable to the fluid rinse device;

a second port coupleable to a pressurized carrier source; and an outlet port coupleable to the sample processing components wherein the controller operates the valve assembly to intermittently open and close the first and second ports; and a controller coupled to the valve assembly to intermittently supply fluid to rinse the sample processing components.

11. The analytical instrument of claim 10 wherein the sample processing components include a sample metering assembly and the valve assembly includes an outlet port coupleable to the sample metering assembly.

12. The analytical instrument of claim 10 wherein the sample processing components include a sampling needle and the valve assembly includes an outlet port coupleable to the sampling needle.

* * * * *